United States Patent [19]

Takiyama et al.

[11] 3,993,663
[45] Nov. 23, 1976

[54] CURABLE RESINOUS COMPOSITION

[75] Inventors: Eiichiro Takiyama, Kamakura; Toshiaki Sugimoto; Toshiaki Hanyuda, both of Yokohama, all of Japan

[73] Assignee: Showa High Polymer Co., Ltd., Tokyo, Japan

[22] Filed: Dec. 27, 1974

[21] Appl. No.: 536,914

[52] U.S. Cl. .................... 260/340.7; 204/159.22; 260/867; 260/875; 526/266
[51] Int. Cl.² ................ C07D 317/04; C08F 24/00
[58] Field of Search ............ 260/867, 340.7, 86.1 R; 526/266

[56] References Cited
UNITED STATES PATENTS

| | | | |
|---|---|---|---|
| 2,687,407 | 8/1954 | Orth | 260/88.3 |
| 2,975,156 | 3/1961 | Fekete | 260/67 |
| 3,087,918 | 4/1963 | Guest et al. | 260/88.3 |
| 3,247,282 | 4/1966 | Englisch et al. | 260/827 |
| 3,291,860 | 12/1966 | Nordstrom | 260/866 |
| 3,296,337 | 1/1967 | Zimmerman | 260/867 |
| 3,468,857 | 9/1969 | Graver et al. | 260/80.3 |

FOREIGN PATENTS OR APPLICATIONS

| | | | |
|---|---|---|---|
| 757,573 | 9/1956 | United Kingdom | 260/867 |
| 955,036 | 4/1964 | United Kingdom | 260/867 |

*Primary Examiner*—Harold D. Anderson
*Assistant Examiner*—Earl A. Nielsen
*Attorney, Agent, or Firm*—Wenderoth, Lind & Ponack

[57] ABSTRACT

This invention relates to a curable resinous composition prepared by reacting 1 mol of (a) an unsaturated polycycloacetal, 0.1 to 3 mols of (b) an ester of polyhydric alcohol/unsaturated monocarboxylic acid, having an alcoholic hydroxyl group and a polymerizable unsaturated bond selected from the group of acryl and methacryl groups in the same molecule, and 0.1 to 2.9 mols (per hydroxyl group in component b) of (c) a polyhydroxy compound.

3 Claims, No Drawings

CURABLE RESINOUS COMPOSITION

This invention relates to an improvement of the invention disclosed in our commonly assigned copending U.S. Pat. application Ser. No. 407,626 filed on Oct. 18, 1973, now U.S. Pat. 3,933,857.

This invention relates to a curable resinous composition, more particularly a curable resinous composition prepared by reacting (a) an unsaturated polycyloacetal, (b) an ester of polyhydric alcohol/ unsaturated monocarboxylic acid, having an alcoholic hydroxyl group and a polymerizable unsaturated bond in the same molecule, and (c) a polyhydroxy compound.

Cycloacetal compounds prepared by the condensation of polyhydric alcohols such as pentaerythritol and sorbitol with unsaturated aldehydes such as crotonaldehyde and acrolein are well known as spiroacetal resins. Among them, diallylidene pentaerythritol prepared by the condensation of pentaerythritol with acrolein, and triallylidene sorbitol prepared by the condensation of sorbitol with acrolein, are valuable since the double bond in their structures has a special reactivity, and it is well known that they react with the active hydrogens of polycarboxylic acids, polyhydric alcohols, polythiokols or phenols to produce thermoplastic or thermosetting resins.

However, such a double bond is not always satisfactory in respect to radical polymerizability, and the reactivity with the active hydrogen of an amine is poor. Consequently, these facts lessen their useful value.

We have studied the various properties of these cycloacetal groups, and found that they can be modified so as to have satisfactory radical polymerizability without damaging their essential features by incorporating acrylic or methacrylic groups therein. This modification of the cycloacetal is based on the fact that a double bond in the cycloacetal such as diallylidene pentaerythritol and triallylidene sorbitol reacts well with an alcoholic hydroxyl group without coloring, and the fact that unsaturated bonds in acrylic or methacrylic groups polymerize or copolymerize well with the same kind or different kinds of polymerizable monomers. This has been proved by the fact that the reaction of cycloacetal compound with an ester of polyhydric alcohol/unsaturated monocarboxylic acid, having an alcoholic hydroxyl group and a polymerizable unsaturated bond in the same molecule, for example hydroxyethylmethacrylate, trimethylolpropanedimethacrylate and glycerinedimethacrylate, provides an addition monomer in which the alcoholic hydroxyl group in the ester is added to the double bond in the cycloacetal. The above addition reaction is completed without producing substitution reaction products or any other by-products, and accordingly the reaction can easily be carried out in a simple and inexpensive apparatus. An example of the polymerizable cycloacetal addition product prepared by reacting diallylidenepentaerythritol with hydroxyethylmethacrylate is represented by the following chemical formula.

$$CH_2=\overset{CH_3}{\underset{|}{C}}-COOCH_2CH_2OCH_2CH_2CH\underset{O-CH_2}{\overset{O-CH_2}{\diagup}}\underset{CH_2-O}{\overset{CH_2-O}{\diagup}}C\underset{CH_2-O}{\overset{CH_2-O}{\diagup}}CHCH_2CH_2OCH_2CH_2OOC-\underset{|}{\overset{|}{C}}=CH_2$$

Further, the polymerizable cycloacetal addition product prepared by reacting diallylidenepentaerythritol with trimethylolpropanedimethacrylate is represented by the following chemical formula.

$$\begin{array}{c}CH_2=\overset{CH_3}{\underset{|}{C}}-COOCH_2\\C_2H_5-\overset{|}{\underset{|}{C}}-CH_2OCH_2CH_2CH\underset{O-CH_2}{\overset{O-CH_2}{\diagup}}C\underset{CH_2-O}{\overset{CH_2-O}{\diagup}}CHCH_2CH_2OCH_2-\\CH_2=\overset{|}{\underset{|}{C}}-COOCH_2\\CH_3\end{array}$$

$$\begin{array}{c}CH_3\\|\\CH_2OCOC=CH_2\\|\\C-C_2H_5\\|\\CH_2OCOC=CH_2\\|\\CH_3\end{array}$$

These addition products are fully disclosed in our above mentioned U.S. patent application Ser. No. 407,626.

However, the use of these polymerizable cycloacetals alone sometimes produces the disadvantages that a resin obtained therefrom has a low molecular weight, and has a low viscosity. In connection with these disadvantages, when fillers, pigments and the like are mixed with the resin, they are easily separated from the resin and its color becomes uneven. We have found that the above mentioned disadvatages can be removed by admixing a polyhydroxy compound having at least 2 hydroxyl groups in the molecule with the polymerizable cycloacetal. The polymerizable cycloacetal compound thus modified with a polyfunctional hydroxy compound can be used for various purposes, and the range of its use increases over that of the unmodified polymerizable cycloacetal compound. "Hydroxyl group" as used herein does not include the —OH of —COOH.

Thus, one object of this invention is to provide a polymerizable cycloacetal compound comprising (a) an unsaturated polycycloacetal and (b) an ester of polyhydric alcohol/unsaturated monocarboxylic acid, which polymerizable cycloacetal compound is modified with (c) a polyhydroxy compound.

Other polycrotonaldehyde acetals, polyacrolein acetals and the like can be used as polycycloacetal compound(a), and they are synthesized by the Schulz Method disclosed in "Angew. Chem." (vol. 62, No. 5, pp. 105-118, 1950). However, among these acetals, a polyacrolein acetal is preferable in order to obtain the desired product having a light color by reacting with the polymerizable alcoholic ester (b) as disclosed below.

Examples of an ester of glycol/unsaturated monocarboxylic acid or polyhydric alcohol/unsaturated monocarboxylic acid (b) which reacts with polycycloacetal compound (a) include hydroxyethyl (or hydroxypropyl) methacrylate, hydroxyethyl (or hydroxypropyl) acrylate, trimethylolpropanedimethacrylate, trimethylolpropanediacrylate, trimethylolethanedimethacrylate, trimethylolethanediacrylate, glycerinediacrylate, glycerinedimethacrylate, pentaerythritoltriacrylate, pentaerythritoltrimethacrylate and the like. The ester (b) must have at least one alcoholic hydroxyl group and at least one unsaturated bond selected from the group of acryl and methacryl groups in the same molecule. An unsaturated alcohol such as allylalcohol is not suitable for this invention since it does not polymerize well at room temperature.

Examples of a suitable polyhydroxy compound (c) having at least two hydroxyl groups in the molecule include polyols, polyethers, polyesters and the like, more particularly various polyhydric alcohols, polyethylene glycol, polypropylene glycol, a blockpolymer of polyethylene glycol/polypropylene glycol, a hydroxy polyester having a terminal hydroxyl group or one in a branch chain, polybutadiene having a terminal hydroxy group, and the like. These compounds are selected optionally depending on the desired use.

A novel curable resinous composition of this invention is prepared by reacting 1 mol of (a) an unsaturated polycycloacetal, 0.1 − 3 mols of (b) an ester of polyhydric alcohol/unsaturated monocarboxylic acid, having an alcoholic hydroxyl group and at least one polymerizable unsaturated bond selected from the group of acryl and methacryl groups in the same molecule, and 0.1 − 2.9 mols (per hydroxyl group in component b) of (c) a polyhydroxy compound. After the reaction is completed, an excess amount of component (b) may be removed, but the removal depends on the use of the reaction product and is not always necessary. The rate of reaction among the three components (a), (b) and (c) is preferably more than 80%. If the reaction rate is below this value, the curing of the product sometimes becomes degraded. The reaction among the three components takes place smoothly without using a solvent, and accordingly it is economically advantageous to carry out the reaction without using a solvent. However, in some cases it may be convenient to carry out a reaction in the presence of a solvent to use the reaction product for paint, adhesive, FRP and the like as it is. During reaction among the three components, there is a possibility that gelation sometimes takes place. So, it is preferable to carry out the reaction in an inert atmosphere rather than in the air. However, such a gelation can be prevented if a polymerization inhibitor such as hydroquinone, benzoquinone, copper salts or the like is used. The inhibitor is used in an amount of 0.001 − 0.1 weight part per 100 weight parts of the total reactants. In order to accelerate the reaction, a small amount of acidic catalyst is required, and a suitable acidic catalyst employed for this purpose includes paratoluene sulfonic acid, diethyl sulfate, ethylsulfonic acid, $BF_3$-ether complex and the like. Among these catalysts, paratoluene sulfonic acid is inexpensive and satisfactory. The amount of the catalyst used is 0.1 − 1.0 weight part per 100 weight parts of the total reactants. If the amount of the catalyst used is less than the above value, the reaction takes much longer and is not economical. On the other hand, if the amount is more than the above value, there is a possibility that coloring or a sub-reaction will take place. From this point of view, the generally preferable amount of catalyst is 0.2 − 0.5 weight part. The reaction temperature may be selected from a range of 50° to 140° C, but the preferable reaction temperature range is from 60° to 110° C for the purpose of preventing coloring or an unfavorable sub-reaction. In order to make the rate of reaction more than 80%, the reaction takes about 12 hours at 80° C.

The reaction product obtained by the present invention, for example, cycloacetal ether poly(metha)-acrylate is very useful as a starting material for synthetic resin or as a modifier. One of the characteristics of the reaction product of this invention is that it generally has a low viscosity of a range of several to several hundred poises without being diluted with other polymerizable monomers, and contains a polyfunctional monomer or oligomer as a main component. Moreover, this reaction product is easily polymerized and cured by the action of a commercially available radical generator such as benzoylperoxide, a combination of cobalt naphthenate with ketoneperoxide or hydroperoxide, azobisisbutyronitrile, benzoinisopropylether, and the like. The resinous composition of this invention is also cured by an electron beam or ultraviolet rays. Commercially available polyesters must be diluted with polymerizable monomers such as styrene in order to obtain such a low viscosity. The same situation applies to commercially available epoxyacryls. Consequently, the shrinkage ratio of curing of commercially available starting materials is larger than that of the product of this invention. This property makes the product of this invention useful as a starting material for FRP (fiberglass reinforced plastics), adhesives, casting materials, paints and the like. Moreover, the product of this invention has an excellent weather resistance and chemical resistance, particularly alkali-resistance, due to the acetal structure contained therein.

Any kind of polymerizable monomer such as a styrene type monomer as well as acrylic type and methacrylic type monomers can be used as a diluent to dilute the product of this invention, and the cured product of this invention retains an excellent strength, weather resistance, chemical resistance and adhesiveness, regardless of such a diluent. As compared with a commercially available anaerobic one-package type adhesive (typical of which is polyethyleneglycol dimethacrylate), an anaerobic adhesive having an excellent adhesiveness, heat-resistance, weather resistance and chemical resistance is prepared by using the polymerizable cycloacetal ether methacrylate, regardless of monomers. This is a significant property since monomers which can be used with commercially available unsaturated polyesters are limited to styrene, diallylphthalate and the like. Thus, the product of this invention improves the weather resistance of conventional epoxy-acrylate resins. In addition to the above mentioned advantages, a fire-retardant and smokeless resin can be obtained by using a halogen-containing polyhydric alcohol, hydroxyl polyester or the like as polyhydroxy compound (c). Moreover, the resinous composition of this invention may be used as a polymerizable plasticizer for thermoplastic resins such as PVC, ABS and the like in the same manner as polyethyleneglycoldimethacrylate, and it has been proved that the former is more excellent in heat-resistance, weather resistance and compatibility than the latter. Thus, the product of this invention has various uses since it has a cycloacetal structure and low viscosity, and is highly polymerizable.

This invention is illustrated by the following examples, but is not restricted thereto.

EXAMPLE 1

260 g of hydroxyethylmethacrylate, 212 g of diallylidenepentaerythritol, 1.5 g of para-toluenesulfonic acid and 0.25 g of hydroquinone were placed in a one liter three-necked flask equipped with a flux condenser, stirrer, thermometer and inlet tube for nitrogen gas. The mixture in the flask was stirred in an atmosphere of nitrogen, and reacted at a temperature of 85°– 90° C for 10 hours. It was proved by an infrared ray absorption spectrum determination that more than 90 – 91 % of the reactants had reacted to produce a light yellowish resin having a low viscosity of 2.7 poises at 25° C. The reaction product was a polymerizable cycloacetal resin (A) having the following formula:

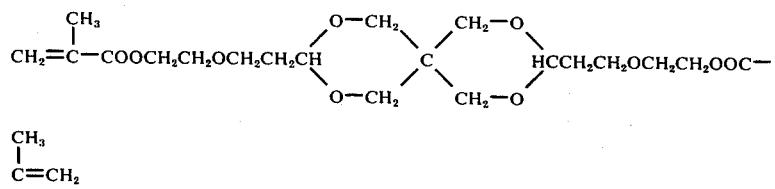

The resin (A) was easily cured in the presence of benzoylperoxide and dimethylaniline to form a transparent product having a high toughness. The cured product had a heat-distortion temperature of 105° C, bending strength of 10.4 kg/mm$^2$, Rockwell hardness of H-98, and degree of shrinkage of 5.8 %.

Both the resin (A) diluted with 40 % of styrene and that diluted with 40 % of methylmethacrylate were also easily cured in the presence of benzoylperoxide and dimethylaniline. The cured product of the former had a bending strength of 10.9 kg/mm$^2$, while that of the latter had a bending strength of 9.4 kg/mm$^2$.

EXAMPLE 2

212 g of diallylidenepentaerythritol, 500 g of trimethylolpropanediacrylate, 2.5 g of para-toluenesulfonic acid and 0.4 g of benzoquinone were placed in the same type of flask as used in Example 1, and were reacted in an atmosphere of nitrogen gas at 80° C for 15 hours. It was proved by an infrared ray absorption spectrum determination that 87 – 90 % of the hydroxyl groups had reacted. The resin (B) thus obtained had a viscosity of 6.5 poises at 25° C. The resin (B) was cured in the same manner as in Example 1 in the presence of benzoylperoxide and dimethylaniline to form a rigid and tough product. 0.5 g of benzoinisopropylether was mixed with 100 g of the resin (B), and the mixture was coated on a glass plate by a knife coater to obtain a film having a thickness of 0.2 mm on the plate. This plate was placed under a high pressure mercury lamp (400 W) positioned at a distance of 10 cm from the film. The resinous film was gelled by 5 seconds' exposure to ultraviolet rays and was completely cured after 30 seconds' exposure. The pencil hardness of the cured film was 3H.

EXAMPLE 3

424 g of diallylidenepentaerythritol, 236 g of hydrogenated bisphenol, 295 g of hydroxypropylmethacrylate, 3.6 g of naphthalene sulfonic acid, and 0.3 g of benzoquinone were placed in a two liter four-necked flask equipped with a flux cooling tuber stirrer, thermometer and inlet tube for nitrogen gas. The mixture was reacted in an atmosphere of nitrogen at a temperature of 90°– 100° C for 5 hours. According to an infrared ray absorption spectrum determination, 92 % of the hydroxyl groups had reacted. The reaction product was neutralized with 2N KOH-alcohol solution, and was then washed with hot water. The washed product was then dried under vacuum to obtain an oily and viscous unsaturated cycloacetal resin (C) having a light yellowish brown color. 100 weight parts of the unsaturated cycloacetal resin (C) were mixed with 150 weight parts of hydrated alumina, and the mixture had a viscosity of about 350 poises. The mixture was cured in the presence of benzoylperoxide at 80° C to obtain a cast plate having a thickness of 3 mm. The cast plate was tested with regard to tracking resistance in accordance with the IEC Method (International Electrotechnical Committee) using 0.1 % NH$_4$Cl solution. Arc-tracking was not formed until more than 51 drops of the NH$_4$Cl solution were dropped on the test sample positioned between two electrodes at 600 V, and at that time the depth of penetration was 0.072 mm. On the other hand, a comparative test sample was prepared mixing 100 parts by weight of hydrogeneted bisphenol containing hexahydrophthalic anhydride as a curing agent with 150 parts by weight of hydrated alumina. The viscosity of the mixture was 530 poises. 1 part by weight of 2,4,6-tris (dimethylaminomethyl) phenol was added to the mixture, which was then cured for 4 hours at 80° C and 6 hours at 120° C. Arc-tracking was not formed until more than 51 drops of the NH$_4$Cl solution were dropped, but the depth of penetration was 0.24 mm. Thus, the regard to the tracking resistance, the resin of this invention was superior to the comparative example. The insulating resistances of the two samples were both 10$^{15}$ — 10$^{16}$ ohm-cm, and the dielectric strengths measured by a step-wise system were both 14 – 16 KV/mm.

EXAMPLE 4

206 g of ethylene glycol, 356 g of diethylene glycol and 498 g of methyltetrahydrophthalic anhydride were placed in a two liter four-necked flask equipped with a fraction condenser, stirrer, thermometer and inlet tube for inert gas. An esterification reaction was carried out under an inert gaseous stream to form a hydroxy polyester having an acid value of 6.2 and a hydroxyl value of 66.9. Then, 880 g of the hydroxy polyester, 424 g of diallylidenepentaerythritol, 330 g of hydroxyethyl acrylate, 4 g of paratoluene sulfonic acid and 0.35 g of hydroquinone were placed in the same type of reactor as used in Example 3, and the mixture was reacted at 90°– 100° C for 6 hours. According to an infrared analysis, it was proved that substantially all of the hydroxyl groups had reacted. When the reaction mixture becomes viscous and is hard to stir at the end of the reaction, the reaction can be continued by adding 200 g of styrene to the reaction mixture. After the reaction had finished, an additional amount of styrene was added in such an amount that the total amount of styrene added became 1100 g, and 3 g of dimedone was dissolved in the reaction product. The resultant product was a light yellowish brown resin (D) having a low viscosity.

100 parts of the resin (D) thus obtained were mixed with 1 part of methylethylketone peroxide and 0.3 part of cobalt naphthenate (Co = 6 %), and the mixture was coated on a steel plate so as to make a coated film of thickness 0.2 mm. The resinous film was gelled in 30 minutes at room temperature, and the stickiness of the film was completely reduced. After 24 hours, the sword hardness of the film reached 36, and it was possible to grind the film. The film was not stripped off the steel plate during a bending test at 90° C.

EXAMPLE 5

550 g of polyether glycol having a molecular weight of 1000–2000 ("Pluronic L-61" sold by Wyandott Co.), 212 g of diallylidenepentaerythritol, 740 g of pentaerythritol trimethacrylate (containing 7 – 8 % of dimethacrylate), 6 g of naphthalene sulfonic acid and 0.4 g of benzoquinone were placed in the same type of flask as used in Example 3. The mixture was reacted for 5 hours at 90° C under an inert stream. According to an infrared analysis, it was proved that 93 % of hydroxyl groups had reacted. To the reaction product, were added 2 g of triethyl amine and then 500 g of diethyleneglycol dimethacrylate to form a resin (E) having a viscosity of about 12 poises.

100 parts of the resin (E) were mixed with 2 parts of cumene hydroperoxide and 0.1 part of dimethyl paratoluidine. The mixture was used as an anaerobic adhesive to bond a bolt to a nut. The bolt was firmly bonded in about 2 hours. After 24 hours, the torque value, at which the bond broke, was 20 ft-lb. Thus, this product is an excellent anaerobic binding agent.

EXAMPLE 6

130 g of dibromoneopentyl glycol, 212 g of diallylidenepentaerythritol, 110 g of hydroxyethyl acrylate, 0.9 g of boron trifluoride ether addition product and 0.2 g of hydroquinone were reacted in the same type of flask as used in Example 1 at 80°– 85° C for 15 hours. 88 – 90 % of hydroxyl groups were found to have reacted. After the reaction, the product was dissolved in 150 g of methylmethacrylate to form a light yellowish brown resinous composition (F) having a viscosity of about 3 poises.

100 parts of the resin (F) thus obtained were mixed with 3 parts of antimony trioxide, and the mixture was cured in the presence of benzoyl peroxide and dimethyl aniline to produce a cast plate. The plate was tested with respect to a flame spread in accordance with ASTM-D-757, and the rate of flame spread was 0.14 inch/min.

In addition to the above test, 100 parts of the resin (F) were mixed with 3 parts of antimony trioxide, 80 parts of hydrated alumina and the above curing agents. The mixture was impregnated in a glass mat (No. 450), and was cured to produce a laminated plate having a glass content of 27 %. The laminated plate was directly contacted with the flame of a heavy oil burner having a flame length of about 50 cm. The plate burned when it was contacted with the flame, but it immediately stopped burning when it was removed from the flame. Although unsaturated polyester produces a large amount of black smoke, the resin of this invention produces only a small amount of light brownish smoke.

EXAMPLE 7

20 parts of methyl methacrylate was mixed with 100 parts of unsaturated cycloacetal resin (A) to prepare resin (G). To this resin (G), was added 15 parts of a copolymer comprising 87 % of vinylchloride, 12 % of vinyl acetate, and 1 % of maleic anhydride to prepare resin (H). The above copolymer was dissolved in tetrahydrofuran to prepare a 40 % solution. These three types of adhesive resinous solutions were used to bond two test pieces made of steel (5 inch long and 1 inch wide) by making an overlapping area 0.5 × 1 inches. The adhesive strength was determined by measuring tensile shear strength, and their results are shown in the following table. In connection with this, it is noted that the resin (G) and (H) were cured by the use of benzoyl peroxide and dimethyl aniline at 30° C.

|  | Adhesive Strength ($kg/cm^2$) | |
| --- | --- | --- |
|  | Ordinary Temperature | 80° C |
| Resin (G) | 114 | 69 |
| Resin (H) | 218 | 131 |
| Copolymer alone | 74 | Substantially zero |

EXAMPLE 8

1000 g of 1,2-polybutadiene having a molecular weight of about 2000 and a hydroxyl group at the end, 212 g of diallylidenepentaerythritol, 290 g of β-hydroxypropyl methacrylate, 4.5 g of paratoluene sulfonic acid, and 0.3 g of hydroquinone were reacted in an inert gaseous stream at 90°– 95° C for 5 hours in a two liter four-necked flask equipped with a cooling tube, stirrer, thermometer and inlet tube for nitrogen gas. According to an infrared ray absorption spectrum analysis, it was proved that 87 % of hydroxyl groups had reacted. When the reaction mixture becomes too viscous to stir the mixture at the end of the reaction, it is possible to control the viscosity of the mixture and to continue the reaction by adding 200 g of styrene to the mixture. After finishing the reaction, the reaction product was diluted with additional styrene in such an amount that the total amount of styrene reached 1000 g, to prepare a reddish brown unsaturated spiroacetal resin (I).

The resin (I) cured by heat in the presence of benzoyl peroxide has a degree of elongation of 230 %, and a tensile strength of 74 $kg/cm^2$, and was proved to be an excellent resin for casting.

EXAMPLE 9

Preparation of Resin J-I 260 g of hydroxyethylmethacrylate, 212 g of diallylidene pentaerythritol, 1.5 g of p-toluene sulfonic acid and 0.25 g of hydroquinone were placed in a one liter four-necked flask equipped with a stirrer, thermometer, flux condenser and inlet tube for nitrogen gas, and were reacted at 85°– 90° C for 10 hours with stirring in a nitrogen gas stream. According to an infrared ray absorption spectrum analysis, it was proved that 90 – 91 % of the hydroxyl groups had reacted to produce light yellowish polymerizable cycloacetal resin J-I having a viscosity of 2.7 poises at 25° C. The chemical structure of this product is as follows:

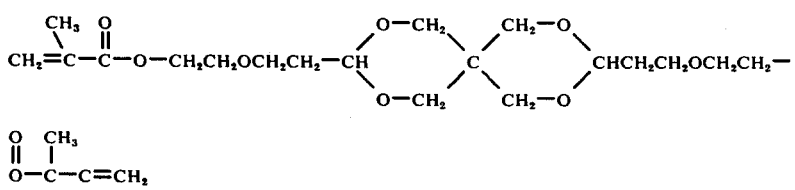

The resin J-I is easily cured in the presence of the curing system of benzoyl peroxide and dimethyl aniline to produce a strong and hard cured product having a heat distortion temperature of 105° C, Rockwell hardness of H-98 and shrinkage of 5.8 %.

A mixture of the resin J-I with 40 % of styrene or 40 % of methylmethacrylate was also easily cured in the presence of benzoyl peroxide and dimethyl aniline. The bending strength of the cured products were respectively 10.9 kg/mm² and 9.4 kg/mm².

Preparation of Resin J-II 300 g of a hydroxyl polyester having a hydroxyl value of 447 and an acid value of 5.2 (prepared from 130 g of hydroxyethylmethacrylate, 1 mol of tetrahydrophthalic anhydride, 1 mol of maleic anhydride, 0.1 mol of diethylene glycol and 3 mols of allylglycidyl ether); 212 g of diallylidene pentaerythritol; 2 g of p-toluene sulfonic acid; and 0.2 g of benzoquinone were reacted with stirring at 90°– 95° C for 8 hours in a nitrogen stream in the same type of flask as used in preparing resin J-I. 90 % of the hydroxyl groups reacted to produce a light reddish brown syrupy resin J-II having a viscosity of 800 poises at 25° C.

The following two types of compositions were prepared using the above resins J-I and J-II respectively.

| Composition J-I | Resin J-I | 90 | parts |
| --- | --- | --- | --- |
| | styrene | 10 | " |
| | methylethylketone peroxide | 2 | " |
| | cobalt naphthenate (Co 6%) | 1 | " |
| Composition J-II | Resin J-II | 60 | parts |
| | styrene | 40 | " |
| | methylethylketone peroxide | 2 | " |
| | cobalt naphthenate (Co 6%) | 1 | " |

The above compositions J-I and J-II were coated on steel plate to a thickness of 0.2 mm, and 24 hours after the coating the films were tested in respect of their physical properties. The sword hardnesses of the films were both 45 – 50. However, according to a bending test (JIS K-5400), the composition J-I film failed in wrapping an eight mm diameter bar, while the composition J-II film succeeded in wrapping even a three mm diameter bar. Moreover, the toughness and adhesiveness of the composition J-II film are both better than those of the composition J-I film.

EXAMPLE 10

Preparation of Resin K-I 212 g of diallylidene pentaerythritol, 500 g of trimethylolpropane diacrylate, 2.5 g of p-toluene sulfonic acid and 0.4 g of benzoquinone were reacted at 80° C for 15 minutes in the same type of flask as used in preparing resin J-I. According to an infrared ray absorption spectrum analysis, it was proved that 87 – 90 % of the hydroxyl groups had reacted to produce a resin K-I having a viscosity of 6.5 poises at 25° C. The resin K-I is easily cured in the presence of a curing system of benzoyl peroxide and dimethyl aniline to produce a tough and hard cured product. The resin K-I is also cured in the presence of ultraviolet rays or electron beams. For example, a mixture of 100 g of the resin K-I and 0.5 g of benzoinisopropylether was coated on a glass plate by a knife coater to obtain a film having a thickness of 0.2 mm. This plate was placed under a high pressure mercury lamp (400 W) positioned at a distance of 10 cm from the film. The resinous film was gelled by 5 seconds' exposure to ultraviolet rays, and was completely cured after 30 seconds' exposure. The pencil hardness of the cured film was 3H.

Preparation of Resin K-II 212 g of diallylidene pentaerythritol, 350 g of trimethylolpropane diacrylate, 35 g of pentaerythritol, 2.4 g of p-toluene sulfonic acid and 0.4 g of benzoquinone were reacted at 80° C for 15 hours in the same type of flask as used in preparing resin J-I to prepare a resin K-II having a viscosity of about 8 poises. According to an infrared ray absorption spectrum analysis, it was proved that only about 60 % of the hydroxyl groups had reacted and that a part of the trimethylolpropane diacrylate remained unreacted.

0.5 g of benzoinisopropylether was added to 100 g of the resin K-II, and the mixture was coated on a glass plate by a knife coater to obtain a film having a thickness of 0.2 mm. This plate was placed under a high pressure mercury lamp (400 W) positioned at a distance of 10 cm from the film. The resinous film was gelled by 1 second's exposure to ultraviolet rays, and was completely cured after 30 seconds' exposure. The pencil hardness of the cured film was 3H.

Benzoinisopropylether was added in an amount of 0.5 % to both resin K-I and resin K-II. Each mixture was coated on a steel plate to a thickness of 0.15 mm, and was cured by ultraviolet rays. The cured films were tested with regard to bending strength according to a bending test (JIS K-5400). The film K-I succeeded in wrapping a 6 mm diameter bar, while the film K-II succeeded in wrapping a 3 mm diameter bar. Thus, it was proved that the film K-II has a higher bending strength than the film K-I. Moreover, the toughness and adhesiveness of the film K-II are both better than those of the film K-I.

What we claim is:
1. A curable composition prepared by reacting
   a. an unsaturated polycycloacetal selected from the group consisting of diallylidene pentaerythritol and triallylidene sorbitol,
   b. an ester selected from the group consisting of hydroxyethyl methacrylate, hydroxypropyl methacrylate, hydroxyethyl acrylate, hydroxypropyl acrylate, trimethylolpropanedimethacrylate, trimethylolpropanediacrylate, trimethylolethanedimethacrylate, trimethylolethanediacrylate, glycerinediacrylate, glycerinedimethacrylate, pentaerythritoltriacrylate and pentaerythritoltrimethacrylate, and
   c. a member selected from the group consisting of an alcohol containing at least two hydroxy groups, a polyether containing at least two hydroxy groups and a polyester containing at least two hydroxy groups,
   in a molar ratio of component a : component b : component c of $1 : 0.1 - 3 : 0.1 - 2.9$, the said amount of component c being based on each hydroxy group in component b.

2. A composition according to claim 1, wherein the component c is polyethylene glycol, polypropylene glycol, or a polyethylene glycol/polypropylene glycol block polymer.

3. A composition according to claim 1, wherein the component c is polybutadiene having terminal hydroxy groups.

* * * * *